United States Patent [19]

Winn

[11] 4,049,653
[45] Sept. 20, 1977

[54] HETEROCYCLIC ESTERS OF ALKYLPHENYL BENZOPYRANS

[75] Inventor: Martin Winn, Deerfield, Ill.

[73] Assignee: Abbott Laboratories, North Chicago, Ill.

[21] Appl. No.: 442,033

[22] Filed: Feb. 13, 1974

Related U.S. Application Data

[63] Continuation-in-part of Ser. No. 348,371, April 5, 1973, abandoned.

[51] Int. Cl.² .................................. C07D 295/00
[52] U.S. Cl. ......................... 544/150; 260/239 A; 260/343.44; 260/247.2 R; 260/268 PC; 260/293.58; 260/293.67; 260/293.88; 260/326.43; 260/345.3; 260/553 A; 260/592; 260/613 R; 260/621 F; 424/248.55; 424/267; 424/274
[58] Field of Search .......... 260/247.2, 307 R, 247.2 B

[56] References Cited

U.S. PATENT DOCUMENTS 3,880,885  4/1975  Houlihan et al. ............ 260/247.2 B
B 447,000  2/1976  Hauck et al. ................ 260/247.2 B

*Primary Examiner*—Paul J. Killos
*Attorney, Agent, or Firm*—Robert L. Niblack

[57] ABSTRACT

Heterocyclic esters of benzopyrans represented by the formula

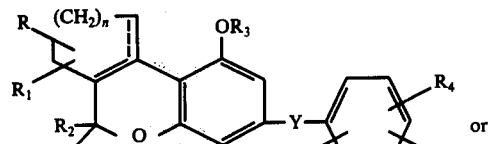

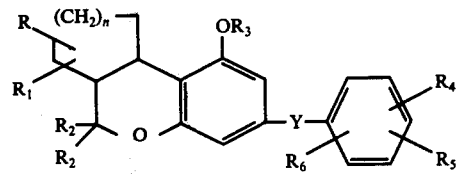

wherein $n$ is 1 or 2; each R and $R_1$ are the same or different members of the group consisting of hydrogen or loweralkyl; $R_2$ is loweralkyl; $R_3$ is

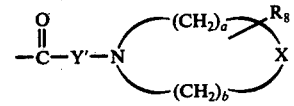

with Y' being a straight or branched chain alkylene group having from one to eight carbon atoms, $a$ is an integer from 1 to 4, $b$ is an integer from 1 to 4, X is $CH_2$, O, S or $NR_7$ with $R_7$ being hydrogen or loweralkyl, with the limitation that when X is O, S, or $NR_7$, $a$ and $b$ each must be 2; $R_8$ is hydrogen or loweralkyl; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable salts thereof.

5 Claims, No Drawings

HETEROCYCLIC ESTERS OF ALKYLPHENYL BENZOPYRANS

REFERENCE TO RELATED APPLICATION

This application is a continuation-in-part of copending application filed Apr. 5, 1973, bearing Ser. No. 348,371 now abandoned.

DETAILED DESCRIPTION OF THE INVENTION

This invention relates to novel benzopyrans and more particularly relates to esters of benzopyrans having an alkylphenyl side chain and having more selective pharmacological actions than the corresponding natural products.

While there are a number of currently available analgesic products, the search for improved analgesic agents has continued for a number of reasons. Aspirin, one of the most effective analgesic agents, does not provide sufficient analgesia to control severe pain such as postoperative pain, pain following certain dental procedures or encountered with toothaches, pain associated with cancer, and the like. A further problem with aspirin is the side effects, particularly the gastrointestinal effects, its ulcergenicity, and the sensitivity which a number of people develop to it. A number of the more potent analgesic agents such as codeine, demoral and morphine have a high addiction liability and are thus classified as narcotics. While one nonaddicting analgesic agent, d-propoxyphene, (Darvon) is available, Darvon does not produce sufficient analgesia to be useful in severe pain states. Darvon further seems to be specific for certain types of pain, and is not effective in all individuals. Therefore, the search for improved, potent, nonaddicting analgesic agents has continued. The present invention provides such agents.

It is also commonly recognized that patients suffering from severe pain, or suffering from pain for any length of time, tend to become anxious and depressed. The compounds of this invention additionally exhibit activity as antianxiety agents. This combination of analgesia and antianxiety activities makes the compounds of this invention particularly useful as a therapeutic group. The compounds of this invention are represented by the formula

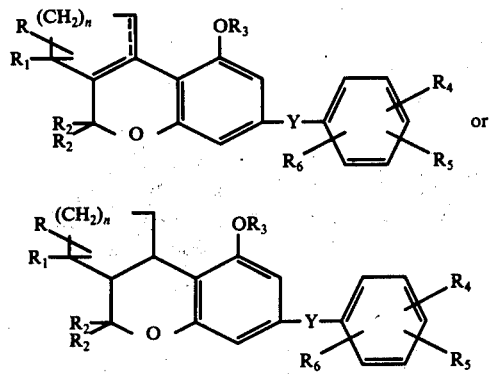

wherein n is 1 or 2; each R and $R_1$ are the same or different members of the group consisting of hydrogen or loweralkyl; $R_2$ is loweralkyl; $R_3$ is

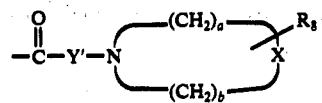

with Y' being a straight or branched chain alkylene group having from one to eight carbon atoms, a is an integer from 1 to 4, b is an integer from 1 to 4, X is $CH_2$, O, S or $NR_7$ with $R_7$ being hydrogen or loweralkyl, with the limitation that when X is O, S or $NR_7$, a and b each must be 2; $R_8$ is hydrogen or loweralkyl; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable salts thereof.

The term "loweralkyl" as used herein, refers to straight and branched chain alkyl radicals of from 1 to 6 carbon atoms such as methyl, ethyl, n-propyl, iso-propyl, n-butyl, sec-butyl, n-pentyl, neo-pentyl, n-hexyl, and the like.

"Halo" includes chloro, fluoro, bromo and iodo.

The term "pharmaceutically acceptable salts" refers to acid addition salts which are those salts, prepared for example, by reacting the basic esters with an organic or inorganic acid, or by reacting the benzopyrans with an acid addition salt of the desired acid. Representative salts include the hydrochloride, hydrobromide, sulfate, bisulfate, acetate, valerate, oleate, laurate, borate, benzoate, lactate, phosphate, tosylate, citrate, maleate, succinate, tartrate and the like. Such salts are well known in the art and are considered to be "pharmaceutically acceptable."

When, for example, n is 1, the compounds are represented by formulae III, IV and V, wherein the side chain

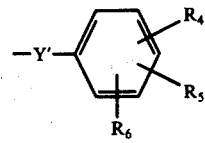

is designated as $R_9$.

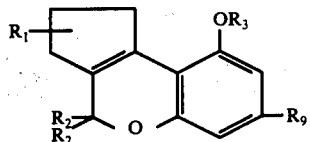

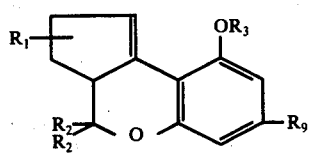

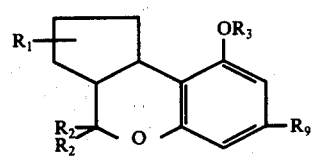

When n is 2, the preferred compounds are represented by formulae VI, VII and VIII.

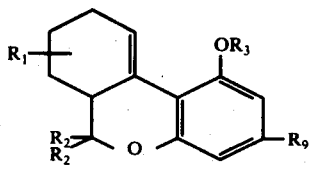

VI

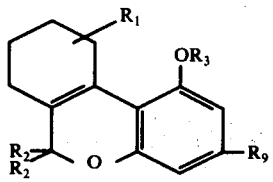

VII

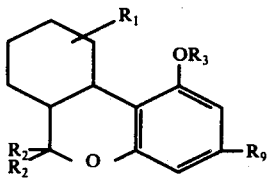

VIII

The compounds of this invention are useful, via oral, parenteral or intravenous administration, as analgesic agents at dosages of from 0.01 to 25.0 mg./kg. of body weight daily. The presently preferred compound, 3-(4-p-fluorophenyl-1-methylbutyl)-1-(4-morpholinobutyryloxy)-6,6,9-trimethyl-7,8,9,10-tetrahydro-6H-dibenzo[b,d]pyran, has an oral $ED_{50}$ of 6.1 in the mouse writhing test for analgesia, [Whittle, Brit. J. Pharmacol., 22 296 (1964) ] (Codeine has an oral $ED_{50}$ of 15.6 mg./kg. in the mouse writhing test), an oral $ED_{50}$ of 5.9 mg./kg. in the rat tail flick test [Harris, et al., J. Pharm. Exp. Ther., 169 17 (1969) ] and an oral $ED_{50}$ of 0.94 mg./kg. in the hot plate test.

In addition to their use as analgesic agents, the compounds are useful as mild tranquilizers at dosages of from 0.01 to 25 mg./kg. of body weight daily. Since many patients suffering from pain are anxious and apprehensive, the compounds of this invention are particularly useful as analgesic agents. The compounds further appear to produce analgesia and mild tranquilization without sedative or sedative-hypnotic effect, thus enabling the patients to carry out their normal activities while taking a compound of this invention.

Generally speaking, the parent compound ($R_3$ is hydrogen) can be prepared according to the following reaction scheme.

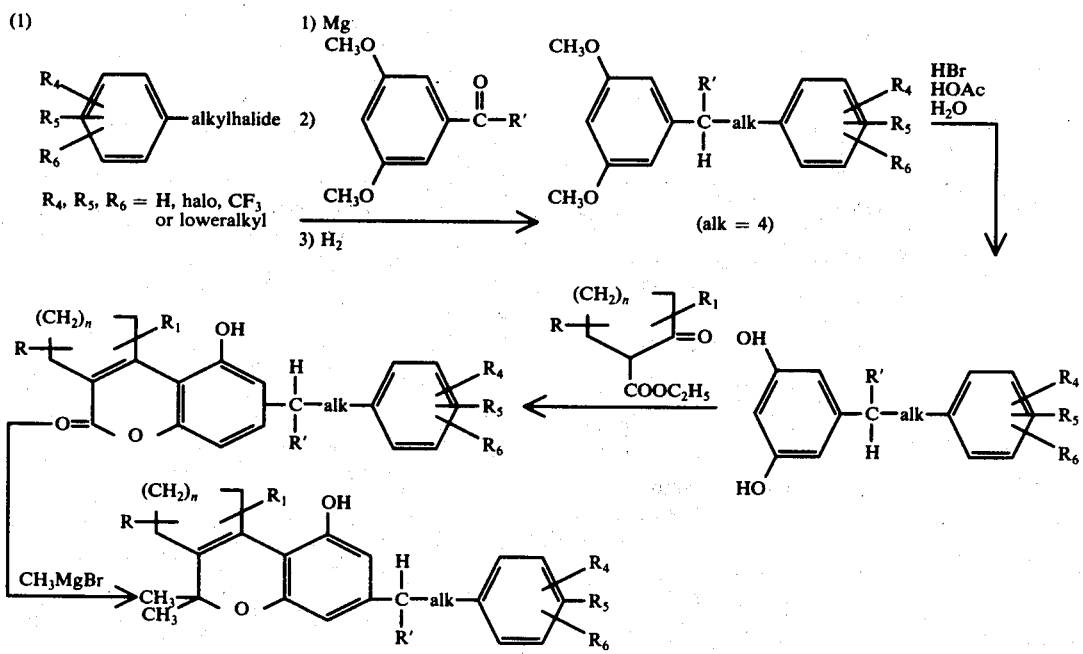

Preferred synthetic routes are represented by the following reaction schemes:

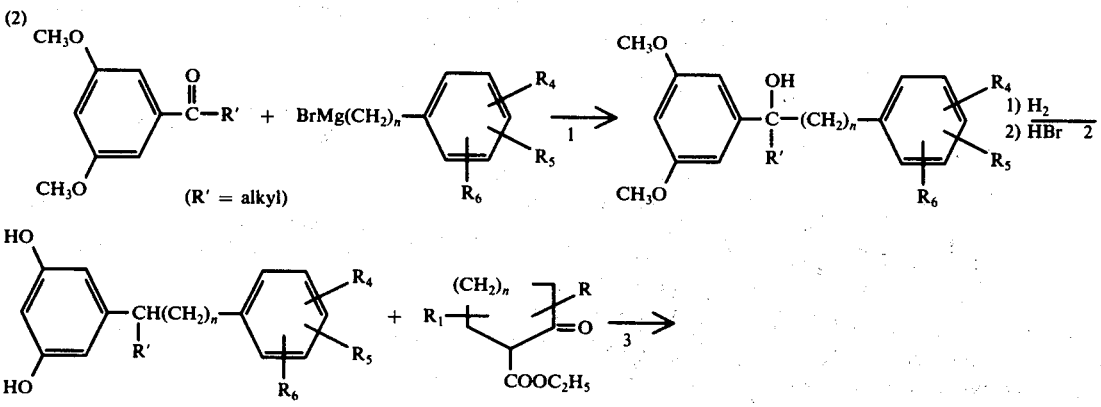

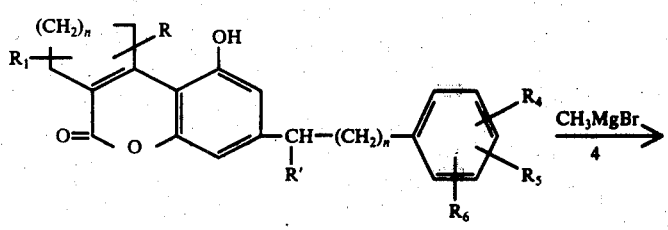

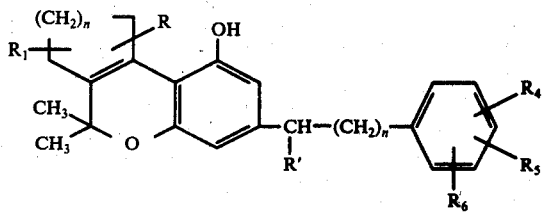

(3)

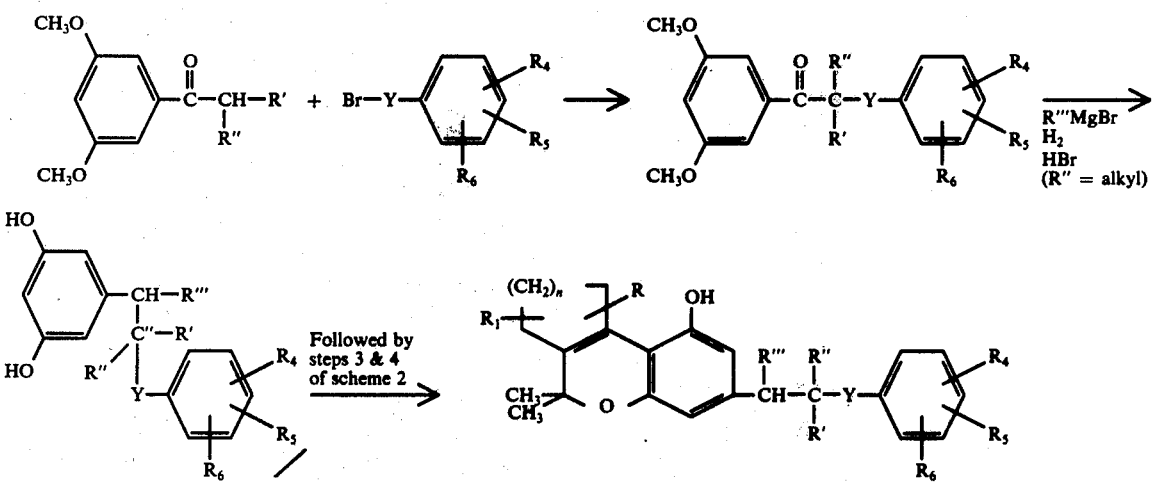

Note: numbers indicate steps

Generally speaking, the esters of this invention are prepared by reacting equimolar quantities of the corresponding hydroxybenzopyran, a carbodiimide, such as for example, dicyclohexyl carbodiimide and the appropriate amino acid or its acid addition salt in a suitable solvent such as methylene chloride, chloroform and the like, for from 2 to 72 hours. The reaction is followed with thin layer chromatography, preferably in 10% methanol/chloroform. The mixture is then cooled in ice and filtered to remove the by-product of dicyclohexylurea. The solvent is evaporated by, for example, employing a vacuum rotary evaporator and the residue is dissolved in, for example, benzene. The solution is filtered again to remove any suspended impurities and the product is either crystallized from suitable solvents such as benzene/ether or the residue can be chromatographed and the product isolated from the appropriate chromatographic fractions. If the basic esters are obtained, the acid addition salts can readily be prepared by reacting the ester with an appropriate organic or inorganic acid. The reaction is represented by the following reaction scheme:

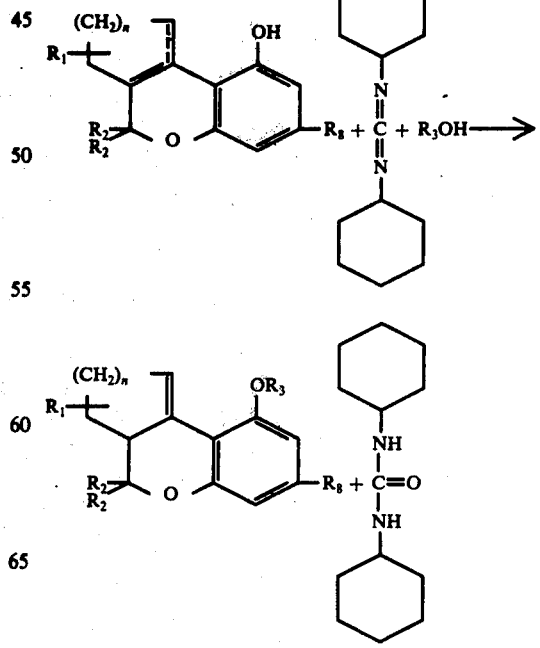

The starting materials can be prepared according to the method described in C. A. 72: 1274 and U.S. Pat. No. 3,639,427.

The following examples further illustrate the present invention:

EXAMPLE 1

Preparation of 2-(3,5-Dimethoxyphenyl)-5-(4-Fluorophenyl)Pentane

A solution of 77 g. of 3-(4-fluorophenyl)propylbromide in 300 ml. of ether was added dropwise over a two hour period to a refluxing solution of 10 g. of magnesium in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl) propylbromide was reacted with 3.5-dimethoxyacetophenone in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-p-fluorophenyl)pentane, b.p. 145 – 155/0.05 mmHg.

Analysis Calcd. for $C_{19}H_{23}O_2F$: C, 75.60; H, 7.69 Found: C, 75.87; H, 7.98.

EXAMPLE 2

Preparation of 2-(3,5-Dihydroxyphenyl)-5-(4-Pentane

Fifty grams of the above-prepared 2-(3,5-dimethoxyphenyl)-5-(4-fluorophenyl)pentane, 450 ml. of acetic acid and 180 ml. of 48% HBr in water were mixed. While cooling, the mixture was saturated with hydrogen bromide gas (approximately ½ hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(4-fluorophenyl)pentane as a brown oil which distills at 180°/0.01 mmHg.

Analysis Calcd. for $C_{17}H_{19}O_2F$: C, 74.20; H, 6.98 Found: C, 73.56; H, 7.04.

EXAMPLE 3

Preparation of 3-(4-p-Fluorophenyl-1-Methylbutyl)-1-Hydroxy-6,6,9-Trimethyl-7,8,9,10-Tetrahydro-6H-Dibenzo[b,d]Pyran Fourteen grams of the above-prepared 2-(3,5-dihydroxyphenyl)-5-(4-fluorophenyl)pentane, 11 g. of ethyl, 4-methyl-2-cyclohexanone-1-carboxylate, 60 ml. of benzene and 3.6 ml. of $POCl_3$ were stirred and refluxed for four hours and stirred at room temperature for 12 hours. The reaction was poured into water and sodium bicarbonate, extracted with ether, dried over magnesium sulfate and concentrated to an oil. The oil was extracted with pentane to remove the unreacted keto ester. The oil was crystallized from acetonitrile to give 3(4-p-fluorophenyl-1-methylbutyl)-1-hydroxy-9-methyl-7,8,9,10-tetrahydro-6H-dibenzo[b,d]pyran-6-one, m.p. 127°– 129° C.

The above pyrone was then dissolved in 80 ml. of ether and added to a methyl magnesium bromide solution prepared from 13 g. of magnesium and 60 g. of methyl bromide in 350 ml. of ether. After refluxing 16 hours, the reaction was worked up with saturated aqueous ammonium chloride solution. The ether layer was separated, concentrated to dryness and the residue was dissolved in 300 ml. of benzene. To the benzene solution was added 0.05 g. of TosOH and the reaction was refluxed for two hours, passing the condensing liquid through 4A molecular sieves. The benzene layer was extracted with sodium bicarbonate in water, concentrated to dryness and dissolved in 500 ml. of pentane. Charcoal was added to the pentane solution and the solution was filtered. The product was then chromatographed on a Florosil activated aluminum magnesium silicate 42 mm × 30 inch column and eluted with 95% pet ether and 5% ethyl ether to yield 10.4 g. of product as a colorless gum.

Analysis Calcd. for $C_{27}H_{33}FO_2$: C, 79.20; H, 8.18 Found: C, 79.36; H, 8.50.

EXAMPLE 4

Preparation of 1-Hydroxy-3-(4-Phenyl-1-Methylbutyl)-6,6,9-Trimethyl-7,8,9,10-Tetrahydro-6H-Dibenzo[b,d]Pyran 1-Hydroxy-3-(4-phenyl-1-methylbutyl)-6,6,9-trimethyl-7,8,9,10-tetrahydro-6H-dibenzo[b,d]pyran was prepared according to the method of Example 3 from 2-(3,5-dihydroxyphenyl)-5-phenylpentane.

EXAMPLE 5

Preparation of 7-(4-p-Fluorophenyl-1-Methylbutyl)-9-Hydroxy-4-Oxo-1,2,3,4-Tetrahydrocyclopenta[c] [1]Benzopyrane Twenty-two grams of 5(1-methyl-4-p-flurophenyl butyl)resorcinol, 80 ml. of benzene, 6 ml. of $POCl_3$, 1 drop of water and 13.0 g. of 2-carbethoxycyclopentanone were refluxed for eight hours and then stirred at room temperature for eight hours. The solution was concentrated in vacuo and the residue taken up in ether and neutralized with potassium bicarbonate solution. The organic phase was dried over $MgSO_4$ and concentrated. The residue was crystallized from $CH_3CN$ to yield 15.6 g. of 7-(4-p-fluorophenyl-1-methylbutyl)-9-hydroxy-4-oxo-1,2,3,4-tetrahydrocyclopenta[c] [1]benzopyran, m.p. 133° – 135° C.

Analysis Calcd. for $C_{23}H_{23}O_3F$: C, 75.50; H, 6.33 Found: C, 75.15; H, 6.21

EXAMPLE 6

Preparation of 4,4-Dimethyl-7-(4-p-Fluorophenyl-1-Methylbutyl)-9-Hydroxy-1,2,3,4-Tetrahydrocyclopenta[c] [1]Benzopyran A solution of 15 g. of the above-prepared pyrone in 30 ml. of ether and 50 ml. of benzene were added slowly to a solution of $CH_3MgBr$ (0.423 mole) in 250 ml. of ether. The reaction was refluxed for 16 hours, and then 500 ml. of a saturated $NH_4Cl$ solution was added slowly. The ether layer was separated, dried over $MgSO_4$ and concentrated. The residue was dissolved in pet ether, decolorized with charcoal and chromatographed on a Florosil activated aluminum magnesium silicate 31 mm × 30 inch column to yield 10.9 g. of product as a pale yellow oil.

Analysis Calcd. for $C_{25}H_{29}O_2F$: C, 78.80; H, 7.70 Found: C, 78.80; H, 7.84

EXAMPLE 7

Preparation of 3-(4-p-Fluorophenyl-1-Methylbutyl)-1-[4-(Piperidino)-Butyryloxy]-6,6,9-Trimethyl-7,8,9,10-Tetrahydro-6H-Dibenzo[b,d]Pyran 3-(4-p-Fluorophenyl-1-methylbutyl)-1-hydroxy-6,6,9-trimethyl-7,8,9,10-tetrahydro-6H-dibenzo[b,d]pyran, (1.603 g.) prepared according to the method of Example 3, was dissolved in 40 ml. of $CH_2Cl_2$, and combined with 0.850 g, of γ-piperidinobutyric acid hydrochloride [m.p. 190°–192°, Cruickshank and Sheehan J. Am. Chem. Soc. 83, 2891 (1961)] and 0.894 g. of dicyclohexylcarbodiimide. The reaction mixture was stirred for 16 hours at room temperature. The insoluble by-product of dicyclohexylurea was separated by filtration and the solution was concentrated in vacuo to yield 2.289 g. of product as a powder. Thin layer chromatography showed one spot with traces of the starting pyran.

Analysis Calcd. for $C_{36}H_{48}NO_3F \cdot HCl \cdot 1\frac{1}{2} H_2O$: C, 68.74; H, 8.41; N, 2.58; Cl, 5.76 Found: C, 69.10; H, 8.38; N, 2.24; Cl, 5.67

EXAMPLE 8

4,4-Dimethyl-7-(4-p-Fluorophenyl-1-Methylbutyl)-9-[4-Piperidino)-Butyryloxy]-1,2,3,4-Tetrahydrocyclopenta[c][1]Benzopyran Hydrochloride 5.56 g. (14.6 mmoles) of 4,4-dimethyl-9-hydroxy-7-(4-p-fluorophenyl-1-methylbutyl)-1,2,3,4-tetrahydrocyclopenta[c][1]benzopyran, prepared according to the method of Example 6, 3.14 g. (15.2 mmoles) of dicyclohexylcarbodiimide and 3.15 g. (15.2 mmoles) of γ-piperidinobutyric acid hydrochloride (m.p. 190°–192°), Cruickshank and Sheehan, J. Am. Chem. Soc. 83, 2891 (1961), are combined with 250 ml. of methylene chloride and stirred for a total of 40 hours at room temperature. The insoluble by-product of dicyclohexylurea is separated by filtration and the methylene chloride is removed using a rotary evaporator. The brown residue is treated with approximately 75 ml. of benzene, and filtered to remove a small amount of insoluble material. The benzene is evaporated and the viscous residue is triturated with about 200 ml. of ether to give the crude product. Recrystallization from benzene yields the desired product.

EXAMPLE 9

4,4-Dimethyl-7-(4-p-Fluorophenyl-1-Methylbutyl)-9-[3-(Piperidino)-Propionyloxy]-1,2,3,4-Tetrahydrocyclopenta[c][1]Benzopyran Hydrochloride 3.12 g. (8.2 mmoles) of 4,4-dimethyl-9-hydroxy-7-(4-p-fluorophenyl-1-methylbutyl)-1,2,3,4-tetrahydrocyclopenta[c][1]benzopyran, prepared according to the method of Example 6, 1.77 g. (8.6 mmoles) of dicyclohexylcarbodiimide and 1.65 g. (8.5 mmoles) of β-piperidinopropionic acid hydrochloride (m.p. 216° – 220°, J. Am. Chem. Soc. 73, 3168 (1951) are combined with 125 ml. of methylene chloride and stirred at room temperature for about 20 hours. The reaction mixture is filtered and the methylene chloride removed using a rotary evaporator. The residue is treated with benzene and filtered to remove a small quantity of insoluble material. The benzene is evaporated and the dark, viscous residue is chromatographed using 100 g. of 60 – 100 mesh Florosil activated magnesium silicate and methanol/chloroform graded solvent mixtures. Chromatography yields an oil which is dissolved in ether and treated with a solution of ethereal HCl. The desired compound appears as crystals which are filtered and washed with additional ether to obtain the desired product.

EXAMPLE 10

1-[4-(Morpholino)Butyryloxy]-3-(4-Phenyl-1-Methylbutyl)-6,6,9-Trimethyl-7,8,9,10-Tetrahydro-6H-Dibenzo[b,d]-Pyran Hydrochloride 0.91 g. (2.33 mmoles) of 1-hydroxy-3-(4-phenyl-1-methylbutyl)-6,6,9-trimethyl-7,8,9,10-tetrahydro-5H-dibenzo[b,d]pyran, prepared according to the method of Example 4, 0.48 g. (2.28 mmoles) of γ-morpholinobutyric acid hydrochloride (Cruickshank and Sheehan, J. Am. Chem. Soc. 83, 2891 (1961), m.p. 180° – 182°) and 0.48 g. (2.35 mmoles) of dicyclohexylcarbodiimide (Aldrich) are combined with 35 ml. of methylene chloride and stirred at room temperature for a total of 40 hours. The insoluble by-product of dicyclohexylurea is removed using a rotary evaporator. The resulting residue is dissolved in about 20 ml. of benzene and a small amount of insoluble material is removed by filtration. The benzene is evaporated and the residue dried in vacuo to give 0.7 g. of material. Crystallization from benzene/pet ether yields the crystalline product.

EXAMPLE 11

4,4-Dimethyl-7-(4-p-Fluorophenyl-1-Methylbutyl)-9-[4-(Morpholino)-Butyryloxy]-1,2,3,4-Tetrahydrocyclopenta[c][1]Benzopyran Hydrochloride 7.10 g. (18.7 mmoles) of 4,4-dimethyl-9-hydroxy-7-(4-p-fluorophenyl-1-methylbutyl)-1,2,3,4-tetrahydrocyclopenta[c][1]benzopyran, prepared according to the method of Example 6, 4.33 g. (21.0 mmoles) of dicyclohexylcarbodiimide and 4.26 g. (20.3 mmoles) of γ-morpholinobutyric acid hydrochloride are combined with 325 ml. of methylene chloride and stirred at room temperature for a total of 24 hours. The insoluble by-product of dicyclohexylurea is separated by filtration and the methylene chloride is removed using a rotary evaporator. The viscous residue is dissolved in about 100 ml. of benzene and the benzene solution is filtered to remove a small amount of insoluble material. The benzene is removed using a rotary evaporator and the remaining residue is triturated with approximately 250 ml. of ether. The solid which forms is filtered, washed with ether and dried to yield a solid. The material is crystallized from benzene/ether to give the solid product.

EXAMPLE 12

4,4-Dimethyl-9-[4-(Morpholino)Butyryloxy]-7-(4-Phenyl-1-Methylbutyl)-1,2,3,4-Tetrahydro-cyclopenta[c][1]Benzopyran Hydrochloride 1.25 g. (3.5 mmoles) of 4,4-dimethyl-9-hydroxy-7-(4-phenyl-1-methylbutyl)-1,2,3,4-tetrahydrocyclopenta[c][1]benzopyran, 0.76 g. (3.63 mmoles) of γ-morpholinobutyric acid hydrochloride and 0.76 g. (3.70 mmoles) of dicyclohexylcarbodiimide are combined in 75 ml. of methylene chloride and stirred at room temperature for 24 hours. The insoluble by-product of dicyclohexylurea is removed by filtration and the methylene chloride solution is concentrated to 20 ml. Cyclohexane is added until the desired compound is obtained as a colorless solid. Recrystallization from methylene chloride/cyclohexane gives the desired crystalline product.

EXAMPLE 13

γ-Pyrrolidinobutyric Acid Hydrochloride 30.0 g. (0.13 mole) of methyl γ-iodobutyrate [F. F. Blicke, W. B. Wright and M. F. Zienty, J. Amer. Chem. Soc. 63, 2488 (1941)] was combined with 36 g. of pyrrolidine (Aldrich) in 300 ml. of benzene, heated at 60° for 0.5 hours and stirred at room temperature for 16 hours. A dark orange layer formed. The benzene solution was decanted, concentrated and distilled (b.p. 100° at 15 mmHg) to give 10 g. of colorless liquid. The infrared and nmr spectra indicated the product to be methyl γ-pyrrolidinobutyrate. This material was dissolved in 100 ml. of 18% hydrochloric acid and heated at reflux for 28 hours. The solution was concentrated under reduced pressure to give a semisolid which was triturated with acetone and filtered. Recrystallization from acetic acid/acetone gave 8.3 g. (33%) of the desired acid hydrochloride as colorless crystals, m.p. 126° – 127°. The infrared and nmr spectra and consistent with the proposed structure.

Analysis Calcd. for $C_8H_{16}ClNO_2$: C, 49.60, H, 8.33; N, 7.28 Found: C, 49.79; H, 8.14; N, 7.21

EXAMPLE 14

4,4-Dimethyl-7-(4-p-Fluorophenyl-1-Methylbutyl)-9-[4-(Pyrrolidino)-Butyryloxy]-1,2,3,4-Tetrahydrocyclopenta[c] [1]Benzopyran Hydrochloride 3.55 g. (9.37 mmoles) of 4,4-dimethyl-9-hydroxy-7-(4-p-fluorophenyl-1-methylbutyl)-1,2,3,4-tetrahydrocyclopenta [c] [1]benzopyran are combined with 1.82 g. (9.37 mmoles) of γ-pyrrolidinobutyric acid hydrochloride and 2.06 g. (10.0 mmoles) of dicyclohexylcarbodiimide in 150 ml. of methylene chloride and stirred at room temperature for 2½ hours. The insoluble by-product of dicyclohexylurea is removed by filtration and the filtrate is evaporated to give a residue which crystallized upon standing. The material is triturated with ether and filtered. Recrystallization from benzene-ether gives the product as colorless crystals.

EXAMPLE 15

γ-Homopiperidinobutyric Acid Hydrochloride 23.0 g. (0.1 mmole) of methyl-γ-iodobutyrate [F. F. Blicke, W. B. Wright and M. F. Zienty, J. Amer. Chem. Soc., 63, 2488 (1941)]was combined with 25.0 g. (0.4 mole) of homopiperidine (Aldrich) and heated at 70° for three hours. The precipitate of amine hydroiodide was removed by filtration and the filtrate was concentrated to an orange oil. The methyl γ-homopiperidinobutyrate distilled as 14.0 g. of colorless liquid at 0.5 mm., b.p. 70° – 71°. This material was dissolved in 75 ml. of aqueous 18% hydrochloric acid solution and heated at reflux for 16 hours. The solution was concentrated under reduced pressure to give a semisolid residue which was triturated with acetone and filtered. Recrystallization from acetic acid/acetone gave 10.0 g. (45%) of product as colorless crystals, m.p. 178° – 179°. The infrared and nmr spectra are consistent with the proposed structure.

Analysis Calcd. for $C_{10}H_{20}ClNO_2$: C, 54.20; H, 9.09; N, 6.32 Found: C, 54.21; H, 8.93; N, 6.26

EXAMPLE 16

4,4-Dimethyl-0-[4-(Homopiperidino)Butyryloxy]-7-(4-Phenyl-1-Methylbutyl)-1,2,3,4-Tetrahydro-cyclopenta-[c] [1]Benzopyran Hydrochloride 4.13 g. (11.7 mmoles) of 4,4-dimethyl-9-hydroxy-7-(4-phenyl-1-methylbutyl)-1,2,3,4-tetrahydrocyclopenta[c][1] benzopyran is combined with 2.6 g. (11.7 mmoles) of γ-homopiperidinobutyric acid hydrochloride ad 2.6 g. (12.5 mmoles) of dicyclohexylcarbodiimide in 175 ml. of methylene chloride and stirred at room temperature for 3.5 hours. The dicyclohexylurea is separated by filtration and the methylene chloride is removed on a rotary evaporator. The residue is dissolved in a methylene chloride/cyclohexane mixture and the small amount of solid which appears is removed by filtration. The solvents are evaporated to give a residue which crystallizes from benzene/ether. Recrystallization gives the product as colorless crystals.

EXAMPLE 17

γ-Morpholinobutyric Acid Hydrobromide 15 g. (0.052 mole) of methyl γ-morpholinobutyrate [Cruickshank and Sheehan, J. Am. Chem. Soc. 83 2891 (1961)] was dissolved in a mixture of 45 ml. of 47% hydrobromic acid and 45 ml. of water and heated for 16 hours at reflux. The solution was taken to dryness under reduced pressure, and the solid which formed was triturated with acetone. The material was filtered and crystallized from 60 ml. of acetic acid to give 12.4 g. (95%) of product as colorless crystals, m.p. 151° – 152.5°. The infrared and nmr spectra are consistent with the proposed structure.

Analysis Calcd. for $C_8H_{16}BrNO_3$: C, 37.81; H, 6.36; Found: C, 37.80; H, 6.28; N, 5.47

EXAMPLES 18–21

The following compounds are prepared according to the method of Example 7 by reacting the appropriate acid with the corresponding hydroxybenzopyran and dicyclohexylcarbodiimide:

4,4-dimethyl-7-(4-fluorophenyl-1-methylbutyl)-9-[5-(piperidino)valeryloxy]-1,2,3,4-tetrahydrocyclopenta[c][1] benzopyran from 4,4-dimethyl-9-hydroxy-7-(4-fluorophenyl-1-methylbutyl)-1,2,3,4-tetrahydrocyclopenta[c]][1]benzopyran and δ-piperidinovaleric acid.

4,4-dimethyl-7-(3-chlorophenyl-n-propyl)-9-(morpholinoacetyloxy)-1,2,3,4-tetrahydrocyclopenta[c][1]-benzopyran tosylate from 4,4-dimethyl-7-(3-chlorophenyl-n-propyl)-9-hydroxyl-1,2,3,4-tetrahydrocyclopenta[c][1]benzopyran and morpholinoacetic acid tosylate.

9-[4-azetidino butyryloxy]-4,4-dimethyl-7-[5(3,5-difluorophenyl)-n-pentyl)]-1,2,3,4-tetrahydrocyclopenta[c][1] benzopyran hydrochloride from 4m4-dimethyl-7-[5-(3,5-difluorophenyl)-n-pentyl]-9-hydroxy-1,2,3,4-tetrahydrocyclopenta[c][1] benzopyran and γ-azetidinobutyric acid hydrochloride.

4,4-dimethyl-7-(4-p-fluorophenyl-1-methylbutyl)-9-[8-(thiomorpholino)-octanoyloxy]-1,2,3,4-tetrhydrocyclopenta [c][1]benzopyran from 4,4-dimethyl-9-hydroxy-7-(4-p-fluorophenyl-1-methylbutyl)-1,2,3,4-tetrahydrocyclopenta[c][1] benzopyran and thiomorpholinooctanoic acid.

EXAMPLE 22

3-(4-Fluorophenyl-1-Methylbutyl)-1-(4-Morpholinobutyryloxy)-6,6,9-Trimethyl-7,8,9,10-Tetrahydro-6H-Dibenzo[b,d]Pyran 7.107 g. 3-(4-fluorophenyl-1-methylbutyl)-1-hydroxy-6,6,9-trimethyl-7,8,9,10-tetrahydro-6H-dibenzo[b,d]pyran, 3.540 g. morpholinobutyric acid hydrochloric and 3.58 g. dicyclohexylcarbodiimide in 125 ml. methylene chloride were stirred at 25° for 18 hours. The dicyclohexylurea which was formed was filtered. The solution was concentrated to 10 ml. and 50 ml. ether added. Cooling gave the product 8.65 g., m.p. 144° – 147°.

Analysis Calcd. for $C_{35}H_{47}ClFNO_4$: C, 70.07; H, 7.88; N, 2.23; CL, 5.92 Found: C, 69.69; H, 8.03; N, 2.35; Cl, 6.38

The present invention includes within its scope pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administraton include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additonally be prepared with enteric coatings.

Liquid dosage forms for oral administration include pharmaceutically acceptable emulsions, solutions, suspensions, syrups and elixirs contaiing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or nonaqueous solutions, suspensions or emulsions. Examples of nonaqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 0.01 to 25 mg./kg. of body weight daily are administered to patients in need of analgesia or tranquilization.

The following example further illustrates the pharmaceutical compositions which are a feature of this invention:

EXAMPLE 23

Tablets weighing 200 mg. and having the following composition are prepared by standard tableting procedures:

| Ingredient | Mg. |
|---|---|
| 3-(4-p-fluorophenyl-1-methylbutyl)-1-[4-(piperidino)-butyryloxy]-6,6,9-trimethyl-7,8,9,10-tetrahydro-6H-dibenzo[b,d]pyran | 100 |
| Starch | 94 |
| Colloidal silica | 5 |
| Magnesium stearate | 1 |

It will be understood by those skilled in the art that the above composition can contain any of the compoulds of this invention.

I claim:

1. A compound of the formula

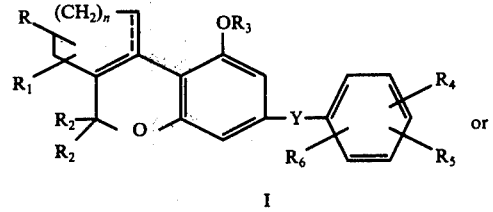

I

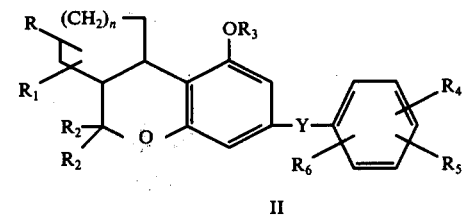

II wherein n is 1 or 2; each R and $R_1$ are the same or different members of the group consisting of hydrogen or loweralkyl; $R_2$ is loweralkyl; $R_3$ is

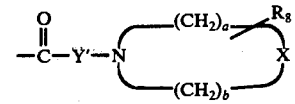

with Y' being a straight or branched chain alkylene group having from one to eight carbon atoms, a is an integer from 1 to 4, b is an integer fro 1 to 4, X is O; $R_8$ is hydrogen or loweralkyl; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable salts thereof.

2. 1-[4(morpholino)butyryloxy]-8-(4-phenyl-1-methylbutyl)-6,6,9-trimethyl-7,8,9,10-tetrahydro-6H-dibenzo[b,d]-pyran hydrochloride.

3. 1-[4-morpholino)butyryloxy]-8-(4-p-fluorophenyl-1-methylbutyl)-6,6,9-trimethyl-7,8,9,10-tetrahydro-6H-dibenzo[b,d]pyran hydrobromide.

4. 4,4-dimethyl-7-(4-p-fluorophenyl-1-methylbutyl)-9-[4-(morpholino)-butyryloxy]-1,2,3,4-tetrahydrocyclopenta[c][l]benzopyran hydrochloride.

5. 4,4-dimethyl-9-[4-(morpholino)butyryloxy]-7-(4-phenyl-1-methylbutyl)-1,2,3,4-tetrahydrocyclopenta[c][l]benzopyran hydrochloride.

* * * * *